(12) United States Patent
Herre

(10) Patent No.: US 6,885,393 B2
(45) Date of Patent: Apr. 26, 2005

(54) ILLUMINATING UNIT FOR AN ARTICLE-SENSING CAMERA

(75) Inventor: Erwin Herre, Moos (DE)

(73) Assignee: Robert Bosch GmbH, Stuttgart (DE)

( * ) Notice: Subject to any disclaimer, the term of this patent is extended or adjusted under 35 U.S.C. 154(b) by 664 days.

(21) Appl. No.: 09/883,389

(22) Filed: Jun. 19, 2001

(65) Prior Publication Data

US 2002/0005892 A1 Jan. 17, 2002

(30) Foreign Application Priority Data

Jun. 28, 2000 (CH) .................................... 2000 1280/00

(51) Int. Cl.⁷ ................................................. H04N 7/18
(52) U.S. Cl. ......................................... 348/125; 348/88
(58) Field of Search ...................... 348/86–95, 125–134, 348/164–168

(56) References Cited

U.S. PATENT DOCUMENTS

| | | | |
|---|---|---|---|
| 4,520,702 A | | 6/1985 | Davis et al. |
| 4,534,470 A | * | 8/1985 | Mills .......................... 209/585 |
| 4,585,947 A | * | 4/1986 | Liptay-Wagner et al. ..................... 250/559.06 |
| 4,882,498 A | | 11/1989 | Cochran et al. |
| 4,972,093 A | | 11/1990 | Cochran et al. |
| 5,072,127 A | | 12/1991 | Cochran et al. |
| 5,172,005 A | * | 12/1992 | Cochran et al. ....... 250/559.08 |
| 5,365,084 A | * | 11/1994 | Cochran et al. ....... 250/559.02 |
| 5,936,353 A | | 8/1999 | Triner et al. |
| 6,697,154 B1 | * | 2/2004 | Owen et al. ............. 356/237.5 |

FOREIGN PATENT DOCUMENTS

| | | |
|---|---|---|
| EP | 0 856 465 | 8/1998 |
| WO | WO 00/70360 A1 | 11/2000 |

* cited by examiner

*Primary Examiner*—Andy Rao
(74) *Attorney, Agent, or Firm*—Venable LLP; Robert Kinberg; Thomas G. Wiseman

(57) ABSTRACT

A conveying system includes a conveyor for advancing items thereon; and an image-capturing apparatus for detecting individual items on the conveyor and for generating image signals representing an image of the items. The image-capturing apparatus includes an illuminating unit formed of a matrix composed of a plurality of light-emitting diodes; a picture-capturing unit for receiving light rays emitted by the matrix and modified by an item situated in a path of the light rays and for generating the image signals; and a control unit connected to the matrix and the picture-capturing unit for a pulsed illumination of the matrix.

15 Claims, 5 Drawing Sheets

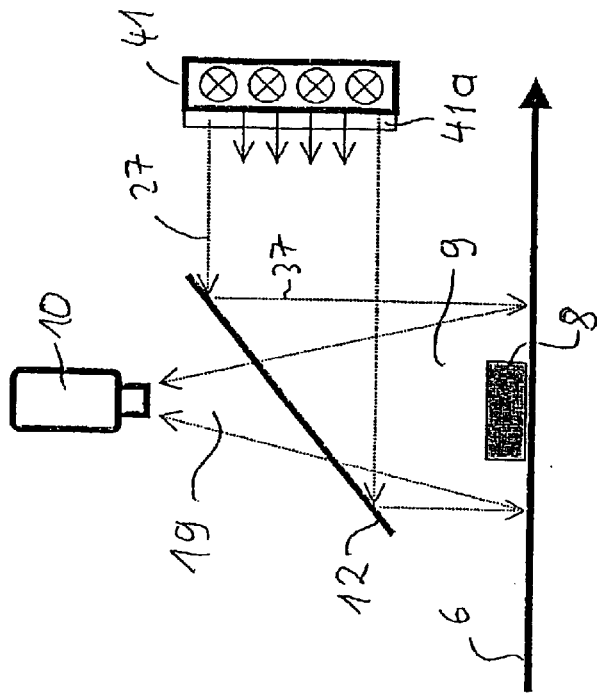
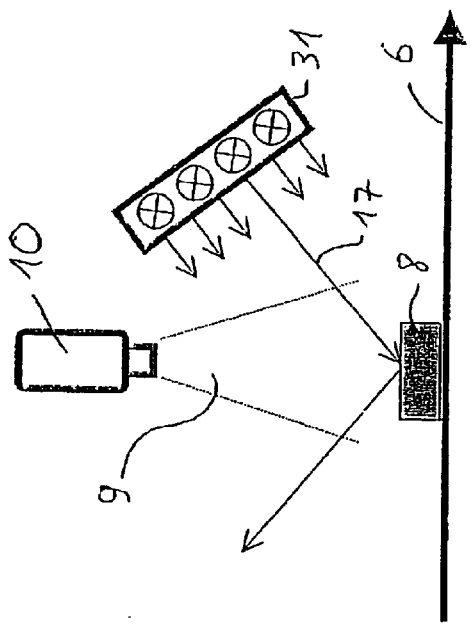
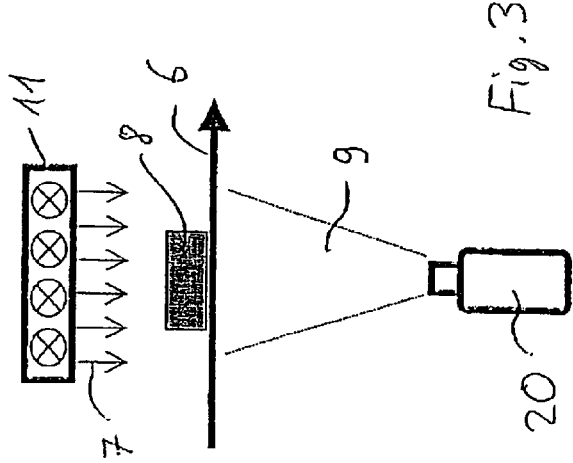
Fig. 5
Fig. 4
Fig. 3

ILLUMINATING UNIT FOR AN ARTICLE-SENSING CAMERA

CROSS REFERENCE TO RELATED APPLICATION

This application claims the priority of Swiss Application No. 2000 1280/00 filed Jun. 28, 2000, which is incorporated herein by reference.

BACKGROUND OF THE INVENTION

This invention relates to an apparatus for forming images of items advanced in an organized or random manner on one or several conveyors. The apparatus has at least one illuminating unit and at least one image-capturing unit (camera) associated with the illuminating unit. The image-capturing unit forms images of the items on the conveyor. The apparatus further includes a control device which controls the illuminating and image-capturing units, for example, in a manner as described in U.S. Pat. Nos. 4,972,093 and 5,936,353.

An apparatus of the above-outlined type is disclosed in European Patent No. 0 856 465 which does not describe any specific illuminating device. An illumination by environmental light has the disadvantage that the reception of the line camera described in the patent may be adversely affected by interfering environmental light effects and thus the article-manipulating gripper devices cannot be accurately controlled.

Conventional illuminating devices have the additional disadvantage that their light sources radiate heat which may lead to a deterioration of the item quality, particularly in case of heat sensitive items such as food products, particularly chocolate or glazed items.

SUMMARY OF THE INVENTION

It is an object of the invention to provide an apparatus of the above-outlined type which improves the quality of the item images without exposing the items to thermal stresses.

This object and others to become apparent as the specification progresses, are accomplished by the invention, according to which, briefly stated, an article-conveying system includes a conveyor for advancing items thereon; and an image-capturing apparatus for detecting individual items on the conveyor and for generating image signals representing an image of the items. The image-capturing apparatus includes an illuminating unit formed of a matrix composed of a plurality of light-emitting diodes; a picture-capturing unit for receiving light rays emitted by the matrix and modified by an item situated in a path of the light rays and for generating the image signals; and a control unit connected to the matrix and the picture-capturing unit for a pulsed illumination of the matrix.

By illuminating a surface occupied by an item and a region adjoining such an item by the light-emitting diode matrix in a homogeneous manner, the recognition zone of the image-capturing unit may be better utilized as concerns the orientation and position of the items. The high degree of efficiency of the light-emitting diode matrix reduces the effect of heat emitted by the illuminating body. Such a heat effect may be further reduced by a pulsed drive of the matrix and, in addition, single-color light-emitting diodes, in conjunction with a suitable color filter arranged in front of the image-capturing unit may further reduce an interference by scattered light.

The light-emitting diodes in the matrix operate either in a transmitted-light mode or in a reflected-light mode. In the former mode the matrix is positioned underneath the item carrying conveyor belt where advantageously the belt serves as a light diffuser. In the reflected-light mode the light is parallelized to produce a directed incident light.

If, as noted earlier, the light-emitting diode matrix, by means of shutter control, emits light only during the image-capturing periods, a pulsed light beam results, whereby a homogenous illumination of the items may be obtained, without the items being exposed to appreciable heat stress. This circumstance therefore allows a positioning of the light-emitting diode matrix closer to the items, whereby the quality of illumination is further improved. At the same time, the short illuminating period permits a very accurate image-capturing of the items even at high item-transporting speeds.

BRIEF DESCRIPTION OF THE DRAWINGS

FIG. 3 is a schematic side elevational view of an embodiment of the invention operating with transmitted light with illumination from above.

FIG. 4 is a schematic side elevational view of an embodiment of the invention operating with reflected light with oblique illumination from above.

FIG. 5 is a schematic side elevational view of an embodiment of the invention operating with reflected light with the interposition of a beam splitter.

DESCRIPTION OF THE PREFERRED EMBODIMENTS

Figure 1:
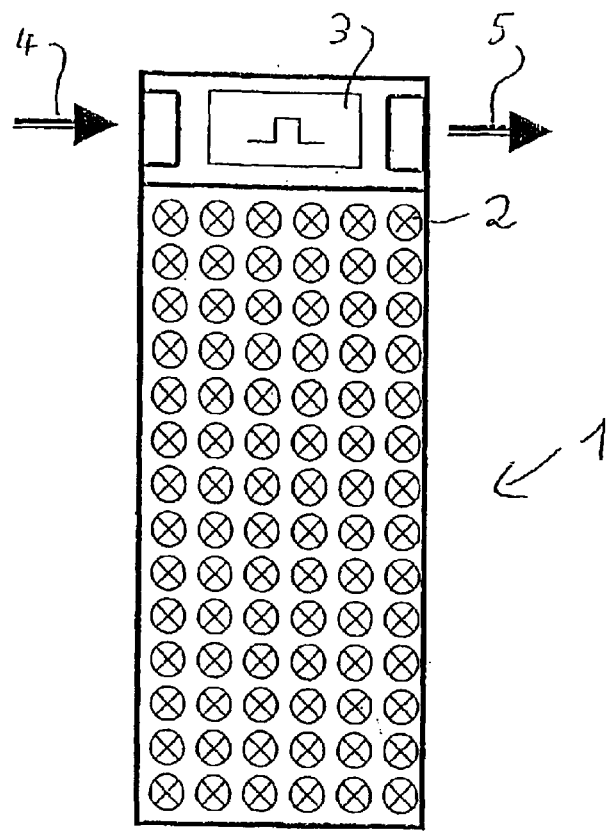
FIG. 1 is a schematic top plan view of a light-emitting diode matrix for use in an apparatus according to the invention.

FIG. 1 shows a light-emitting diode matrix 1 composed of a plurality of light-emitting diodes 2 arranged in rows and columns. For example, there may be provided 432 light-emitting diodes arranged in 12 columns and 36 rows. The light-emitting diodes 2 as viewed together, constitute the light emitting surface. A control circuit 3 is connected to the matrix 1 which is controlled by symbolically illustrated control pulses 4 and which may forward control pulses 5 from an output to a further matrix (not shown) immediately adjoining the matrix 1 for the purpose of increasing the number of matrix columns. Thus, the matrices may be disposed in a cascade connection.

A cascade arrangement is of advantage because control pulses need to be applied only to the first matrix 1; the control pulses are then taken over by the various cascaded matrices. Such control pulses represent, in case of an intermittent operation of the matrix, the duration and timing of the energized state of the light-emitting diodes 2. Advantageously, in a flash operation, the light-emitting diodes 2 are driven synchronously with an image-capturing operation of a camera or imaging unit 10. The duration of a flash period may be 1 ms. In case of a speed of 60 m/min of the conveyor belt 6, the image fuzziness amounts to 1 mm.

A matrix 1 with light-emitting diodes 2 makes possible a pulsed operation of the light-emitting diodes with an illumination period of 0.1 ms. When using a separate voltage supply for the light-emitting diodes 2 and for the signals of the control computer, the control signals are maintained potential-free by means of optical couplers which preferably have limit frequencies of over 100 kHz. It is a further advantage of the light-emitting diodes 2 that they are simple to control by low voltage devices and they age slowly.

The matrix 1 composed of 432 light-emitting diodes as noted above, has a width of 100 mm and a length of 300 mm as viewed in the conveying direction of the conveyor 6. By providing a cascade arrangement of several light-emitting diode matrices the light source may be adapted to any conveyor width. Thus, with eight matrices 1 in cascade connection a conveyor belt surface which is 30 cm long and 80 cm wide may be illuminated.

Preferably, the matrix 1 or interconnected matrices 1 are placed in a protective casing whose top side is of a clear transparent material such as PLEXIGLAS. In the description below, matrix and matrix module (with several matrices) is used interchangeably and provided with the same reference characters. Further, identical reference characters designate identical features. An individual matrix 1 as well as a module has a compact, flat construction.

Figure 2:
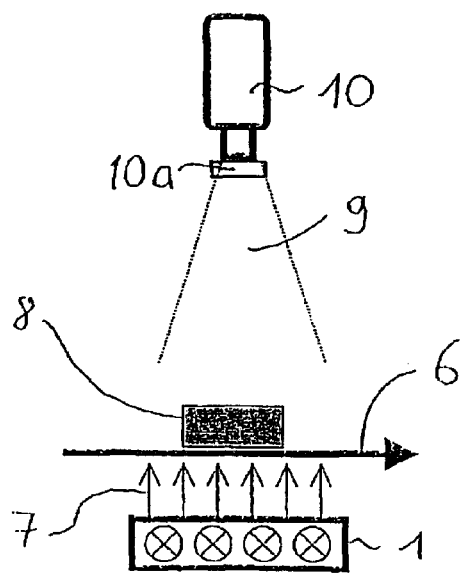
FIG. 2 is a schematic side elevational view of an embodiment of the invention operating with transmitted light with illumination from below.

FIG. 2 shows an arrangement operating with transmitted light. The matrix 1 is positioned underneath the conveyor belt 6 and illuminates the latter from below with parallel light rays 7. The conveyor belt 6 functions as a diffuser. The image-capturing unit (camera) 10 is situated above the conveyor belt 6. The light passing by an item 8 and thus not reflected thereby, is received in the sensor cone 9 of the camera 10 and is subsequently further processed. It is an advantage of this arrangement that the light-emitting diode matrix 1 may be disposed closely under the conveyor belt 6. Based on the short illumination periods (the light-dark ratio may be, for example, 1:100 and the duration of illumination may be 0.2 ms) and the use of light-emitting diodes 2 practically no heat is emitted which could damage the items 8. Further, the light-emitting diodes 2 have a high degree of efficiency. It is further feasible to make the module 1 watertight for removing the generated heat by convection cooling.

The light-emitting diodes 2 may have any desired color, such as close to the infrared range, red, blue, yellow or green. Preferably, all the light-emitting diodes 2 are of the same color. In case no white light-emitting diodes 2 are used but, for example, identical red diodes, that is, monochromatic diodes 2, find application, then in front of the camera 10 a color filter 10a for the same wavelength range may be used. As a result, the camera 10 receives only transmitted light components which essentially originate from the matrix 1. Thus, environmental light effects (except for those in the transparent frequency range) may be further reduced.

FIG. 3 shows an arrangement which operates with transmitted light and which includes a camera 20 situated underneath the conveyor 6. The sensor cone 9 of the camera 20 is directed to the reverse outer face of the conveyor belt 6 and captures the items in transmitted light emitted by a light-emitting diode matrix 11.

FIG. 4 shows a further embodiment operating with reflected light or dark field illumination. A light-emitting diode matrix 31 is positioned obliquely above the sensor range cone 9 of the camera 10 and illuminates the item 8 with a light beam 17. The diffused scattered light enters the camera 10 and is utilized for evaluating the image signal.

FIG. 5 shows a reflecting light arrangement including a beam splitter 12 which is oriented at an angle of 45° to the upper surface of the conveyor belt 6. In this preferred arrangement the light-emitting diode matrix 41 is oriented perpendicularly to the conveyor belt 6. An optical element 41a is positioned at the output of the matrix 41 to obtain a paralellized incident light beam 27. The latter is deflected by the beam splitter 12 to obtain a beam 37 with parallel rays. After the beam 37 impinges on the item 8 and the conveyor belt 6, the reflected light is received by the sensing cone 9 of the camera 10. A portion 19 of the reflected light passes through the beam splitter 12 toward the camera 10. The remaining part of the rays reflected from the item 8 and the belt 6 is reflected back by the beam splitter 12 to the light-emitting diode matrix 41.

Figure 6:
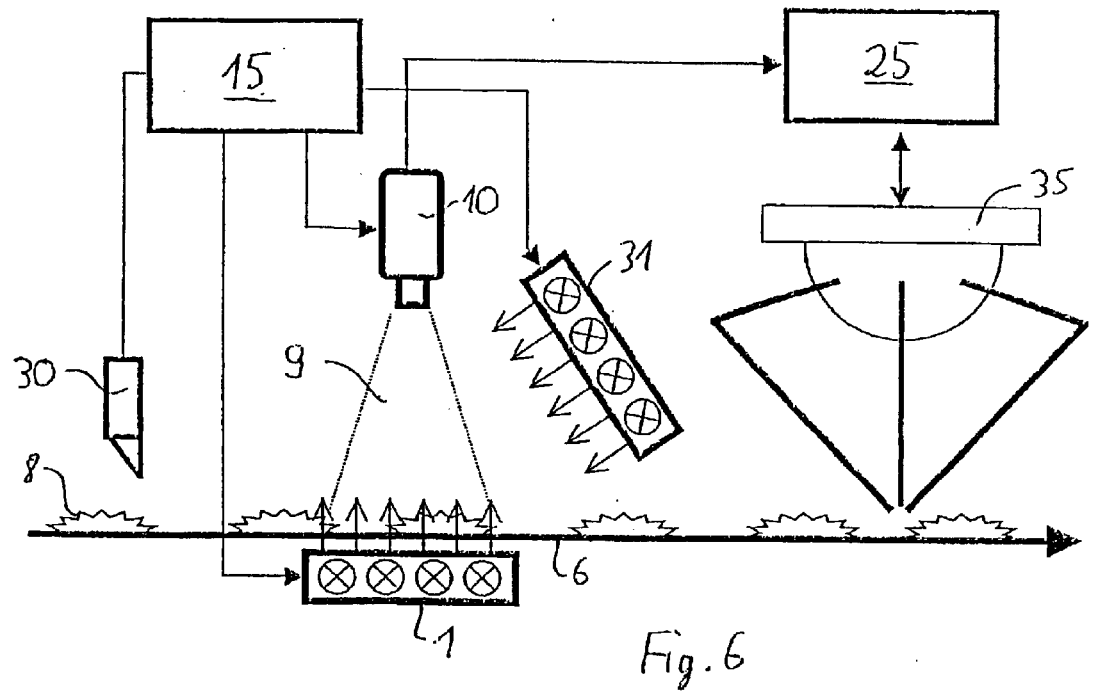
FIG. 6 is a schematic side elevational view of an embodiment which is in part a combination of the embodiments of FIGS. 2 and 4 and which further shows a gripper control.

FIG. 6 schematically shows an assembly which operates with transmitted and reflected light. An item sensor 30 detects the passage of an item 8 and transmits a signal to a regulating device 15 which also serves as a control device for the light-emitting diode matrix 1 situated underneath the conveyor belt 6 and the light-emitting diode matrix 31 positioned obliquely above the conveyor belt 6. At the same time, the regulating device 15 receives image signals generated by the camera 10 based on image signals received from the sensor cone 9. The camera 10 transmits the signals to a control device 25 operating a gripper 35. Such a gripper may be a multi-arm assembly as described, for example, in European Patent No. 0 250 470. The camera 10 first receives transmitted light signals and, for example, 16–40 ms later it receives reflected light signals. It is to be understood that the sequence of the received transmitted and reflected light signals may have a reverse sequence.

Figure 7:
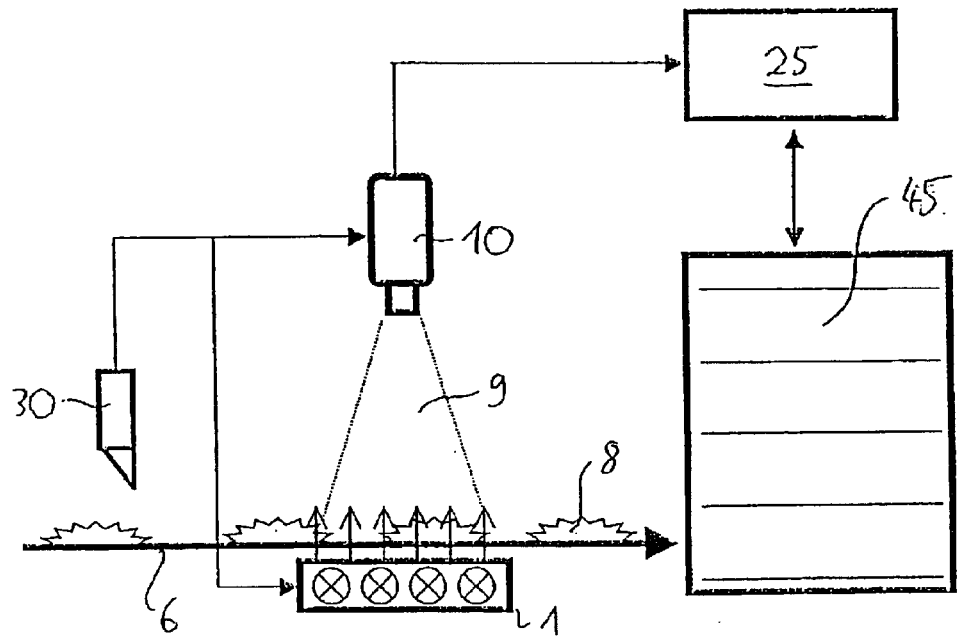
FIG. 7 is schematic side elevational view of an embodiment generally according to the arrangement of FIG. 2, including an item storage control.

In the FIG. 7 arrangement only a transmitted light is used and the signals received by the camera 10 are applied to the control device 25 which controls a storage device for distributing the incoming items 8. The camera 10 may be an apparatus which detects the position and dimension of the items 8 and which serves as a supply system for storing items or for controlling an item wrapping machine or the like.

A synchronous control of the camera 10 and the light-emitting diode matrix 1 is effected by a system control 15 shown in FIG. 6 but not shown in FIG. 7.

Figure 8:
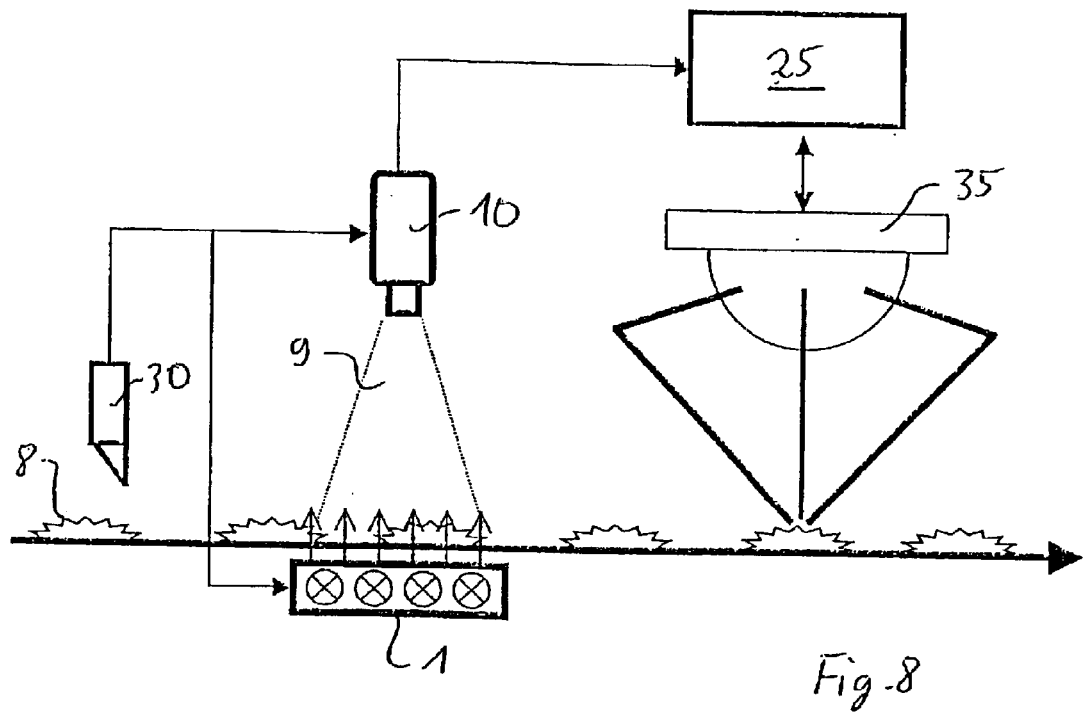
FIG. 8 is a schematic side elevational view of an embodiment generally according to the arrangement of FIG. 2, further showing a gripper control.
Figure 9:
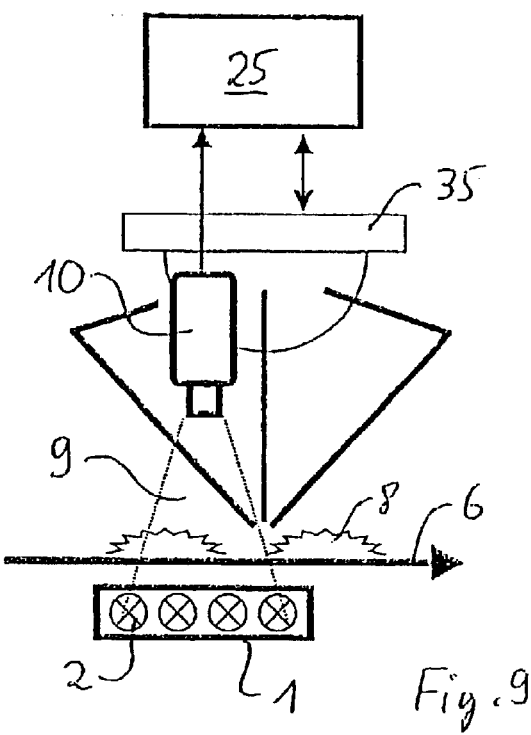
FIG. 9 is a schematic side elevational view of an embodiment of the invention generally according to the arrangement of FIG. 2, wherein such arrangement is disposed in the operational zone of a gripper.

FIG. 8 shows a further embodiment with which the gripper 35 is controlled with precision by means of a simple transmitted light process. This embodiment is a simplification of the FIG. 6 arrangement, inasmuch as no reflected light is used. FIG. 9 shows an arrangement where the camera 10 is positioned in the working zone of the gripper 35. By means of a suitable logic system of the control device 25 either the shadows emanating from the gripper 35 may be eliminated by computation with the aid of several images or suitable exposures are taken only if no mechanical component (arm or gripper part) of the gripper 35 protrudes into that portion of the sensor cone 9 which is to be evaluated. In this manner the respective location of the items 8 in the working zone may be directly and timely predicted. As a result, a gripper 35 operating with high precision and having a very small spatial requirement may be obtained. In such a case, between the housing of the light-emitting diode matrix 1 and the conveyor belt 6 preferably a transparent plate, for example, a glass plate is inserted which protects the light-emitting diode matrix 1 from the gripper and its grasping device.

Figure 10:
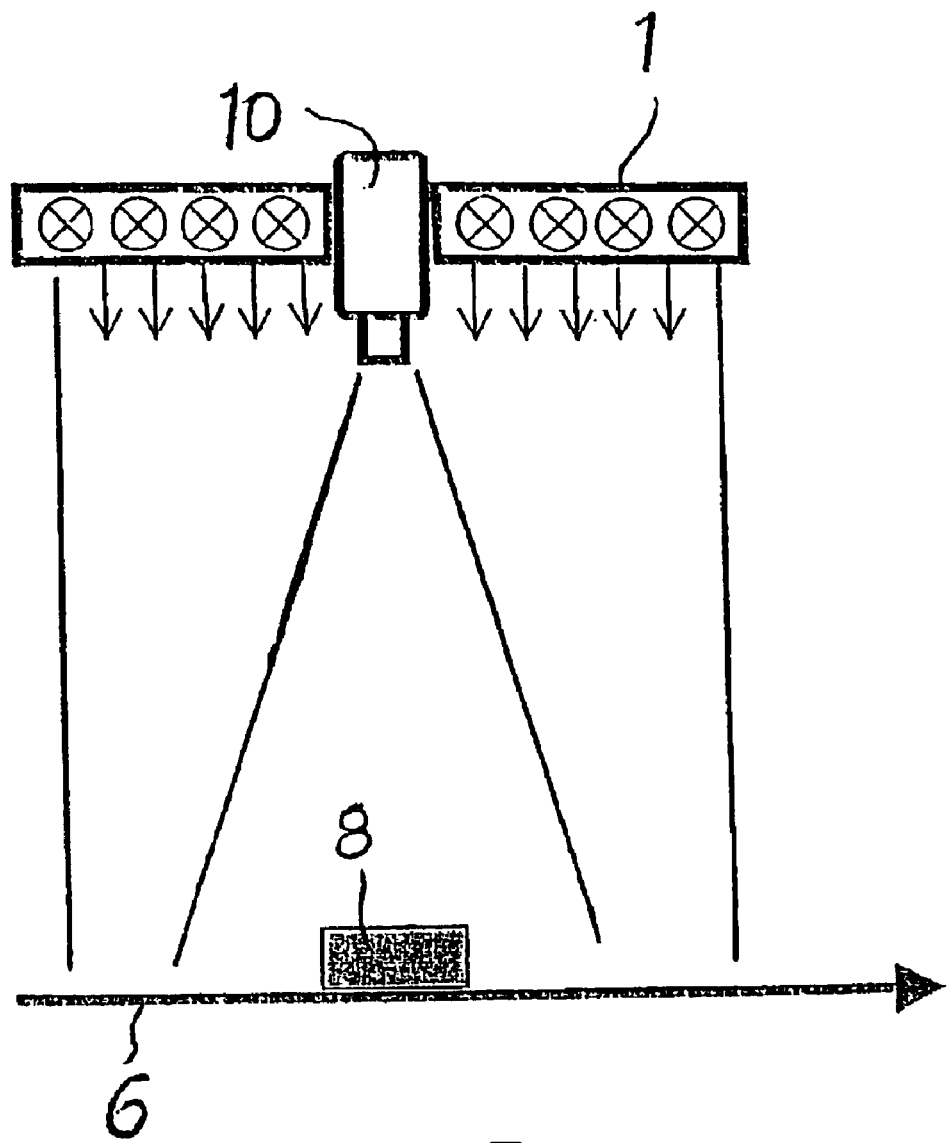
FIG. 10 is a schematic side elevational view of an embodiment of the invention operating with reflected light and with a camera located in the center of the light-emitting diode matrix.

In the embodiment according to FIG. 10 the camera 10 i9s flanked or at least partially surrounded by the light-emitting diode matrix 1 such that the camera 10 is centrally disposed with respect to the light-emitting diode matrix.

It is noted that by a combination of reflected light and transmitted light with a synchronized flash illumination in short intervals of typically 16–40 ms the contour of the item 8 may be determined from transmitted light and additional properties may be obtained from the reflected light image. It is to be understood that for both of these aspects a separate, individual camera may be used. Also, the above-described individual devices may be combined with the described individual features.

It will be understood that the above description of the present invention is susceptible to various modifications, changes and adaptations, and the same are intended to be comprehended within the meaning and range of equivalents of the appended claims.

What is claimed is:

1. A conveying system comprising
   (a) conveyor for advancing items thereon; and
   (b) an image-capturing apparatus for detecting individual items on the conveyor and for generating image signals representing an image of the items; the apparatus including
      (1) an illuminating unit formed of a matrix composed of a plurality of light-emitting diodes;
      (2) a picture-capturing unit for receiving light rays emitted by said matrix and modified by an item situated in a path of the light rays and for generating the image signals; and
      (3) a control unit connected to said matrix and said picture-capturing unit for a pulsed illumination of said matrix and for synchronizing the pulsed illumination of said matrix with actuation of said picture-capturing unit for individually capturing images of the items such that said light-emitting diode matrix only emits light during picture-capturing periods of the picture-capturing unit.

2. The system as defined in claim 1, wherein said light-emitting diodes are monochromatic; further comprising a filter positioned in front of said picture-capturing unit in the path of said light rays; said filter transmitting light solely of a wavelength range of said light-emitting diodes.

3. The system as defined in claim 1, wherein said matrix is positioned above said conveyor and said picture-capturing unit is disposed below said conveyor, whereby said image-capturing apparatus operates with transmitted light.

4. The system as defined in claim 1, wherein said matrix is positioned below said conveyor and said picture-capturing unit is disposed above said conveyor, whereby said image-capturing apparatus operates with transmitted light; further wherein said conveyor is a light-diffusing belt.

5. The system as defined in claim 1, wherein said matrix and said picture-capturing unit are disposed above said conveyor, whereby said image-capturing apparatus operates with reflected light.

6. The system as defined in claim 5, further comprising an optical element at an output of said matrix for parallelizing light rays emitted by said matrix.

7. The system as defined in claim 5, further comprising a reflector positioned between said matrix and said conveyor for deflecting the light rays, emitted by said matrix, toward said conveyor.

8. The system as defined in claim 5, wherein said picture-capturing unit is disposed centrally in said matrix.

9. A conveying system comprising
   (a) a conveyor for advancing items thereon; and
   (b) an image-capturing apparatus for detecting individual items on the conveyor and for generating image signals representing an image of the items; the apparatus including
      (1) an illuminating unit including
         (i) a first matrix composed of light-emitting diodes and disposed above said conveyor;
         (ii) a second matrix composed of a plurality of light-emitting diodes and disposed below said conveyor,
      (2) a picture-capturing unit disposed above said conveyor for receiving light rays emitted by said first and second matrices in reflected and transmitted light, respectively, and modified by an item situated in a part of the light rays and for generating the image signals; and
      (3) a control unit connected to said first and second matrices and said picture-capturing unit for a pulsed illumination of said first and second matrices and for synchronizing the pulsed illumination of said first and second matrices with actuation of said picture-capturing unit for individually capturing images of the items such that said light-emitting diode matrix only emits light during picture-capturing periods of the picture capturing unit.

10. The system as defined in claim 1, wherein the system comprises a control device operating a gripper for gripping said items and wherein the picture-capturing unit transmits a signal based on a captured picture to the control device.

11. The system as defined in claim 1, wherein the system comprises a control device which controls a storage device for distributing said items and wherein the picture-capturing unit transmits a signal based on a captured picture to the control device.

12. The system as defined in claim 9, wherein the system comprises a control device operating a gripper for gripping said items and wherein the picture-capturing unit transmits a signal based on a captured picture to the control device.

13. The system as defined in claim 9, wherein the system comprises a control device which controls a storage device for distributing said items and wherein the picture-capturing unit transmits a signal based on a captured picture to the control device.

14. The system as defined in claim 1, wherein said light-emitting diode matrix is controlled by a shutter-control of the picture-capturing unit.

15. The system as defined in claim 9, wherein said light-emitting diode matrix is controlled by a shutter-control of the picture-capturing unit.

* * * * *